(12) United States Patent
Gerhardt et al.

(10) Patent No.: US 10,426,171 B2
(45) Date of Patent: Oct. 1, 2019

(54) METHODS FOR PROPHYLAXIS OF INFECTIONS IN CROPS AND ORNAMENTALS, PREFERABLY IN VITICULTURE, AND IN WOODY PLANTS

(71) Applicant: BIOPRACT GMBH, Berlin (DE)

(72) Inventors: Matthias Gerhardt, Berlin (DE); Joachim Pheiffer, Wilnsdorf (DE); Hanns-Heinz Kassemeyer, Pfaffenweiler (DE); Rene Fuchs, Herzhausen (DE); Sophie Jacobs, Giessen (DE)

(73) Assignee: BIOPRACT GMBH, Berlin (DE)

( * ) Notice: Subject to any disclaimer, the term of this patent is extended or adjusted under 35 U.S.C. 154(b) by 91 days.

(21) Appl. No.: 15/323,419

(22) PCT Filed: Jun. 16, 2015

(86) PCT No.: PCT/DE2015/000289
§ 371 (c)(1),
(2) Date: Jan. 1, 2017

(87) PCT Pub. No.: WO2016/000671
PCT Pub. Date: Jan. 7, 2016

(65) Prior Publication Data
US 2017/0156342 A1    Jun. 8, 2017

(30) Foreign Application Priority Data
Jul. 3, 2014  (DE) .................. 10 2014 009 813

(51) Int. Cl.
*A01N 63/00*   (2006.01)
*A01N 63/02*   (2006.01)
*A01N 25/02*   (2006.01)

(52) U.S. Cl.
CPC ............. *A01N 63/00* (2013.01); *A01N 25/02* (2013.01); *A01N 63/02* (2013.01); *C12Y 304/21* (2013.01)

(58) Field of Classification Search
None
See application file for complete search history.

(56) References Cited

U.S. PATENT DOCUMENTS

2008/0248558 A1 * 10/2008 Deinhammer ............ B08B 7/00
435/264

FOREIGN PATENT DOCUMENTS

| CN | 101 514 331 |  | 8/2009 |
|----|----|----|----|
| CN | 103 461 383 |  | 12/2013 |
| DE | 10 2005 04852 |  | 4/2007 |
| JP | S54 73182 |  | 6/1979 |
| JP | S57 85307 |  | 5/1982 |
| JP | 2011177105 |  | 9/2011 |
| KR | 20100116562 A | * | 11/2010 |
| WO | WO 91/02459 |  | 3/1991 |
| WO | WO 01/30161 |  | 5/2001 |

OTHER PUBLICATIONS

BD, BD Tryptic Soy Broth (TSB) package insert; Becton Dickinson GmbH: Heidelberg, Germany; pp. 1-3. (Year: 2014).*

Dunne, C., Moënne-Loccoz, Y., de Bruijn, F.J. and O'Gara, F., 2000. Overproduction of an inducible extracellular serine protease improves biological control of Pythium ultimum by Stenotrophomonas maltophilia strain W81. Microbiology, 146(8), pp. 2069-2078.

* cited by examiner

*Primary Examiner* — Michelle F. Paguio Frising
(74) *Attorney, Agent, or Firm* — JMB Davis Ben-David

(57) ABSTRACT

The invention concerns a method for prophylaxis of infections by fungi, particularly by oomycetes, and of bacterial infections in crop and ornamental plants. Areas of application are vine, fruit, vegetable and ornamental plant growing. The method of the invention is characterized in that an aqueous solution of a protease, alone or in combination with ß-glucanases and/or chitinases, is prepared, stabilizers, stickers and wetters are added, and the additized solution is applied by conventional techniques to the plants a number of times within the vegetation period, preferably ahead of weather-related phases of high infection threat.

16 Claims, 4 Drawing Sheets

METHODS FOR PROPHYLAXIS OF INFECTIONS IN CROPS AND ORNAMENTALS, PREFERABLY IN VITICULTURE, AND IN WOODY PLANTS

CROSS-REFERENCE TO RELATED APPLICATIONS

This is the U.S. National Stage of International Application No. PCT/DE2015/000289, filed Jun. 16, 2015, which was published in German under PCT Article 21(2), which in turn claims the benefit of German Patent Application No. 10 2014 009 813.3, filed Jul. 3, 2014.

FIELD

The invention relates to a method for prophylaxis of infections caused by fungi, in particular oomycetes, as well as to prophylaxis of bacterial infections in crops and ornamental plants. Areas of application are vegetable, fruit, vine and ornamental plant growing, preferably vine and vegetable growing.

BACKGROUND

Plant diseases in crop and ornamental plants as well as in woody plants lead annually to high economic losses. Also, in hydroponic vegetable and ornamental plant growing in greenhouses, fungi and oomycetes such as *Phytophthora*, *Pythium* and *Peronospora* play an important role as cause for plant diseases (Malathrakis & Goumas, 1999; Paulitz & Berlanger, 2001). In vegetable (in particular potato and tomato), fruit, ornamental plant and vine growing as well as in forestry, they are of particular economical relevance. In 2013, potatoes were globally grown at an agriculturally used area of 19.3 million hectare (Food and Agriculture Organization of the United Nations, Statistics Division). The most important pathogen in potato growing, which has gained even more importance by expanding plant growing into warmer climates, is the oomycete *Phytophthora infestans*, the pathogen that causes late blight (Oerke and Steiner, 1996). Its spreading is only controllable by the constant use of fungicides (more than 235 million US $ per year only for potato growing). The total market just for fungicides amounts to 5.5 billion US $ per year (Powell & Jutsum, 1993).

In Germany, approximately 100 million euros are spent annually only for the pest management in viticulture (Ochßner, 2009). In ecological viticulture, solely copper-containing plant protection products are used. However, these products are environmentally hazardous and potentially toxic. For this reason, it is of great interest to establish alternative, improved means of protection that are effective against pathogens and simultaneously ecologically friendly.

Here, the propagation cycle of oomycetes will be described using the example of *Plasmopara viticola*, which causes grapevine downy mildew. The life cycle is divided into two sections of varying epidemiological significance. The oospore, which is important for the survival of the pathogen during winter, is formed in the sexual phase. During the asexual summer cycle, large quantities of sporangia are released. *Plasmopara viticola* hibernates as oospore in the soil in leaf debris of heavily infested leafs. During late winter, the oospores become germinable and maintain their germination capacity until early summer. As soon as the soil warms up and sufficient precipitation has fallen, they germinate and form primary sporangia. Until mid-June, oospores keep germinating during heavy rains. Some oospores may also be dormant for more than a year and germinate in the following year. Usually, germination and release of zoospores originates from the primary sporangium when temperatures rise above 10° C. and more than 8 mm precipitation has fallen. Under these conditions, usually the first young leaves of grapevine are unfolded, so that the primary infection can take place. For the primary infection by the germinated zoospores, the leaves have to be sufficiently wetted with water. Solely in this phase, the infection can be prevented or reduced if damaging or inhibiting the zoospores has been successful.

The primary infection is the starting point of the summer cycle of *Plasmopara viticola*, in which the pathogen reproduces asexually by sporangia and may cause epidemics if the conditions for reproducing are favourable. The primary infection is followed by the incubation time, in which the pathogen matures inside the leaf without visible symptoms. A treatment of the infection is no longer possible at that time. Growth and development of the pathogen are heavily dependent on temperature, so that at higher temperatures the leaf tissue is faster penetrated by the mycelium and the oil spots appear earlier in comparison to low temperatures. At the end of the incubation time, so-called oil spots appear as a visible symptom of the fungal infection. As soon as at night the relative humidity rises above 95% and the temperatures remain above 12° C., sporangiophores protrude from the stomata of the infected lamina. The sporangia are spread by drops of water or movement of air. As soon as these drops of water contact a green part of their host plant, the zoospores hatch. Hatching of zoospores and subsequent infection occurs under optimal conditions at 24° C. within four hours. If the temperatures are lower or higher, hatching of zoospores is delayed and the process of infection is prolonged. *Plasmopara viticola* may infect leaves, inflorescence including stems, grapes and shoot tips if they have stomata and if they are wetted. Small drops of water are already sufficient for the infection, however, the conditions of infection are more favourable if the wetting with water is extensive and persists for a long time. After each infection, again an incubation time follows and, subsequently, sporangia will spread as soon as there is sufficient humidity at night. *Plasmopara viticola* belongs to the polycyclic pathogens and can undergo several propagation cycles during one growing season. If optimal conditions for the spreading of sporangia and for infections remain during longer periods and the incubation times are short due to the temperature conditions, an epidemic can develop rapidly. Drought delays the spread of *Plasmopara viticola* and impedes the progression of epidemics. It is possible to predict locally phases of high risk of an infection and, consequently, to take specific prophylactic preventive measures.

Under the climatic conditions prevalent in central Europe, infections by such pathogens are to be expected in every year. To what extent these infections lead to epidemics is highly dependent on the annual weather conditions, and is not predictable at the beginning of the growing period. Epidemics, for example of grapevine downy mildew (*Plasmopara viticola*), can become very severe in highly susceptible classical grape varieties within a few rainy days. Therefore, this infection has to be detected and controlled at an early stage. If the infestation is already in an advanced stage, a later control is no longer possible. For this reason, commercial plant growing is only possible with preventive measures against such infections. A forecasting method, which allows performing specifically preventive controls, was already developed for *Plasmopara viticola* at the German federal institute for viticulture (Staatliches Weinbauinstitut) and put into practice.

Currently, numerous fungicides are on offer for conventional plant growing. Solely in viticulture, 29 fungicides are approved for application in grapevine downy mildew at present.

For ecological vine growing, grapevine downy mildew is a challenge, since here a preventive treatment is indispensable and currently only copper-containing preparations (e.g. Cuprozin) are approved. Because of the known ecotoxicological concerns regarding copper, there is an urgent need to find alternatives to this agent. These alternatives, however, have to have sufficient efficacy also under high infestation rates. For years, tests have demonstrated that the vast majority of preparations that are approved as plant strengthening agents do not show satisfactory efficacy against grapevine downy mildew. Some plant strengthening agents are effective against grapevine downy mildew at low infestation rates, however, a control measure would not have been necessary here. At a higher infestation rates, which also justify combating from an commercial point of view, the efficacy of the tested preparation was insufficient. From these tests it is perceived that no biological control of grapevine downy mildew is practicable in ecological plant growing. Especially in ecological vine growing with the limited possibility to stop an epidemic, effective and practicable approaches for the biological control of epidemics are urgently needed.

Relevance, Progress and Control of Bacterial Infections

Although the number of plant-pathogenic bacteria is lower than the number of fungi-like pathogens, the damage to crop plants caused by bacterial diseases is very high. Bacteria of the genus *Xanthomonas* globally cause diseases in all main groups of higher plants, which are accompanied by chlorotic and necrotic lesions, wilt and rots. An example with high economic relevance is black rot in varieties of cabbage, which is caused by *Xanthomonas campestris* pv. *campestris*. *Xanthomonas oryzae* pv. *oryzae* leads to white leaves/bacterial blight of rice by infestation of rice plants, which is one of the most serious diseases in rice plants, and subsequently to major economic and social problems. Likewise, mention must be made of *Pathovar X. axonopodis* pv. *citri*, the pathogen that causes citrus cancer, and *X. campestris* pv. *Vesicatoria*, the pathogen that causes bacterial leaf spot disease on peppers and tomatoes which is of economic importance particularly in regions with a warm and humid climate. Furthermore, fire blight, caused by the pathogen *Erwinia amylovora*, which is subject to mandatory reporting, has to be mentioned. Host plants of *E. amylovora* are rosaceae such as apple, pear and quince. *E. amylovora* causes wilt of leaves and blossoms of infested plant, which will then turn brown or black. Moreover, the bacterial species *Pseudomonas syringae*, which causes various plant diseases such as cancer, wilt and spots in important crop plants such as tomato, pepper and soy bean, has to be mentioned. This widespread species is of major importance in many plants grown under glass such as tomato, cucumber and courgette.

Most of the described bacterial plant pathogens belong to the group of proteobacteria and are gram-negative organisms (e.g. *Pseudomonas*, *Xanthomonas*). However, there are also economically relevant gram-positive pathogens such as *Clavibacter michiganensis* ssp. *Michiganensis*, which causes bacterial wilt in tomatoes. This quarantine pest is of major importance in warmer and drier growing regions of tomatoes and in greenhouses.

Plant pathogenic bacteria have several strategies to survive in the environment, for example in soil, in plant material such as seeds or in insects. Insects, other animals and humans play an important role in their spreading. Water, e.g. in form of rain drops, is an important vehicle in respect of the distribution at a plant. If bacteria are transferred to a host plant, they penetrate through natural openings, such as stomata or hydathodes, through lesions of the plant. A high bacterial density as well as external conditions such as rain, high humidity or damaged spots facilitate the infection of a plant. Bacteria can easily multiply in the interior of the plant, they colonize the apoplast and damage from there the whole plant. They disturb the physiology and morphology of plants and thus, they cause disease symptoms such as necrotic spots, defoliation, scabbing, wilt or rot (De la Fuente and Burdman, 2011).

It is therefore crucial to protect crop plants against such bacterial infections and thus to secure their harvest. Various chemical compounds and copper compounds appear on the current list of plant protection agents with an antibacterial effect that are approved in Germany. Copper containing preparations are the only means which, in turn, are allowed for the use in ecological agriculture. Treatments with copper containing preparations for the control of bacteriosis have a partial effect and show their limitations as soon as the density of the bacterial inoculum passes a certain threshold. Due to the known ecotoxicological effects of copper compounds and other agrochemicals, legitimate concerns about the use of such plant protection products exist. Furthermore, even in Germany it is allowed in exceptional cases to use plant protection agents that contain antibiotics such as streptomycin to control fire blight. In other countries, streptomycin is a legitimate means against bacteriosis, but at the same time, the use of antibiotics is extremely questionable as undesirable effects on the environment as well as reductions in efficacy by development of resistance by bacteria may be encountered through undifferentiated use of antibiotics. Therefore, it is urgently needed to develop improved, highly effective and commercially relevant alternatives to these agents that are more environmentally-friendly and safer for the user.

SUMMARY

The invention aims to develop a highly efficient means for controlling infections caused by fungi, in particular oomycetes, and bacterial infections in crop and ornamental plants that is harmless for the plant itself as well as for the ecosystem. The primary objective of the present invention is to develop a method for prophylaxis of infections of crop plants used in agriculture that are caused by phytopathogens. In particular, the problem of recognizing and preventing epidemics such as grapevine downy mildew in wine varieties early shall be solved. Providing appropriate means is also comprised by the invention.

Figure 1:
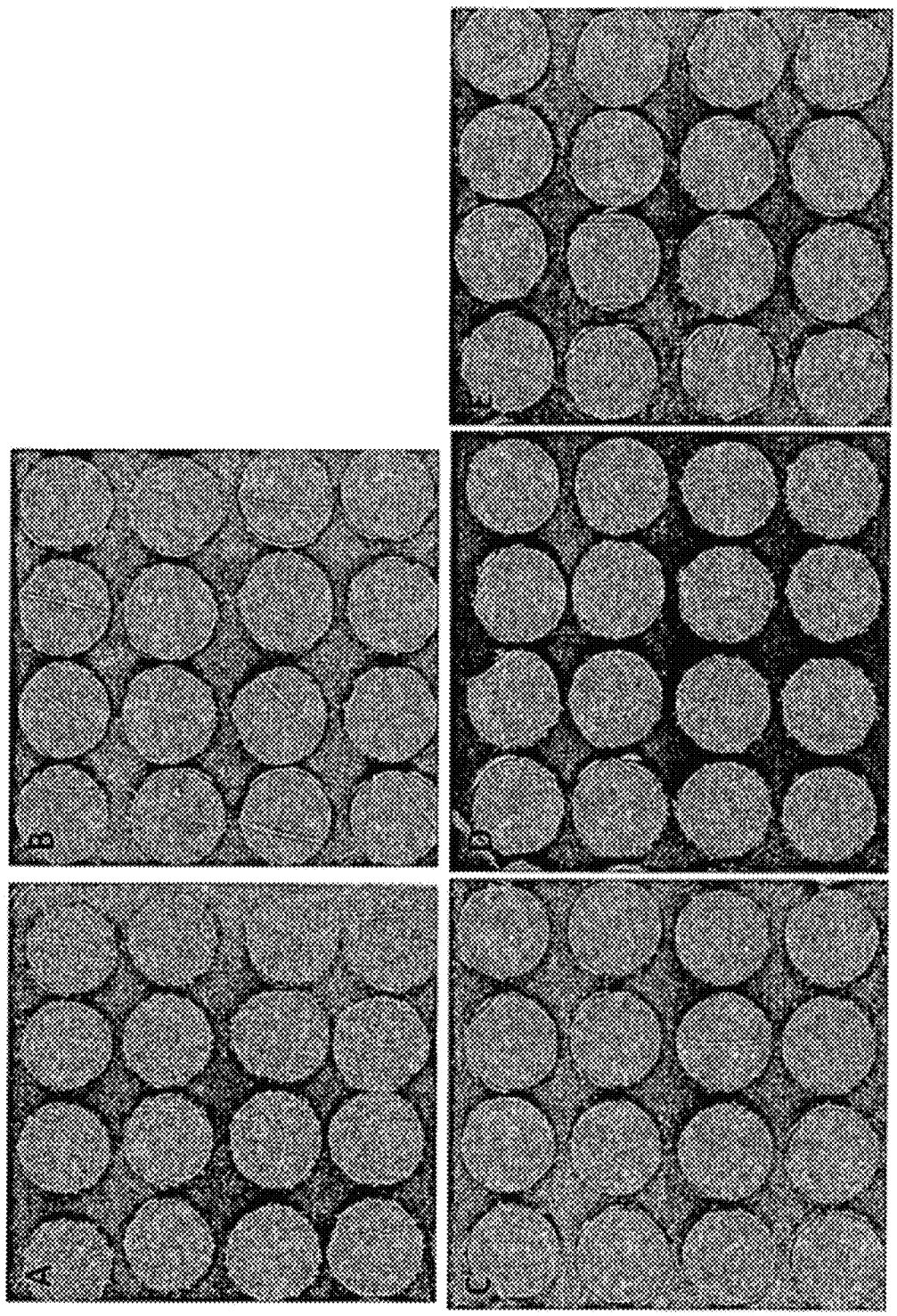
FIG. 1: Shows leaf discs treated with water (A), copper-containing plant protection product (B), protease I (C), protease II (D) or protease III (E).

2. Increasingly, methods of biological and integrated plant protection such as the use of beneficial organisms and pheromones against insects, the use of soil-borne bacterial und fugal antagonists as well as the use of plant extracts are being established. Among the most important antagonistically acting classes of organisms are the bacteria *Bacillus*, *Pseudomonas* and *Streptomyces* and the fungi *Trichoderma*, *Coniothyrium* und *Verticillium*. Of particular importance in this context is the bacterium *Bacillus subtilis* that, as "plant growths promoting rhizobacterium" (PGPR), secretes phytosanitary metabolites, and the fungal genus *Trichoderma*, of which strains are used as "biocontrol agent" (Kücük, C. and M. Kivanc, 2002; DeMarco, J. L., et al., 2003). While many animal pests can be sufficiently controlled by these biological methods, infections caused by oomycetes are only difficult to combat. In the agricultural sector, the following pant diseases are of outstanding importance due to their risk of infection and the resulting losses thereof (Table 1):

TABLE 1

| | Tax. group | Disease | Agricultural area | Examples |
|---|---|---|---|---|
| Fungi | Ascomycota | Powdery mildew | Vegetable, grain, fruit, wine and ornamental plant growing | *Erysiphe necator* (grapevine), *Blumeria graminis* (grain) |
| | Ascomycota | Grey mold | Vegetable, fruit, wine and ornamental plant growing | *Botrytis cinerea* (strawberry, grapevine, etc.) |
| | Basidiomycota | Rusts | Vegetable, grain, fruit and ornamental plant growing | *Puccinia graminis* (grain), *Phakospora pachyrhizi* (soy bean) |
| | Basidiomycota | Smuts | Vegetable, grain, fruit and ornamental plant growing | *Ustilago maydis* (maize), *Ustilago hordei* (barley) |
| Oomycetes | Oomycetes | Downy mildew, late blight | Vegetable, fruit, wine and ornamental plant growing | *Phytophthora infestans* (potato & tomato), *Plasmopara viticola* (grapevine) |
| Bacteria | Proteobacteria | Fire blight, wilt, spots, and others | Vegetable, grain, fruit and ornamental plant growing | *Erwinia amylovorans*, *Pseudomonas syringae*, *Xanthomonas campestris* |
| | Actinomycetes | Wilt and others | Vegetable, grain, fruit and ornamental plant growing | *Clavibacter michiganensis* |

DETAILED DESCRIPTION

I. Current Development of Strategies in Plant Protection

1. The demands on chemical plant protection products in respect of efficacy, selectivity, specificity, biological degradation and efficacy on non-targeted organisms are steadily increasing. In the meantime, a number of novel plant protection products is available that meet these requirements. The use of numerous older compounds, such as hydrocarbons (aldrin, DDT, DDD, dieldrin, kelthane) is forbidden by now. Currently used chemical plant protection products, however, (e.g. ortho-phenylphenol E 231 or thiabendazole E 233) are becoming more and more criticized. They show numerous harmful side effects, which make their use problematic. These include, the damage of the crop plant apart, changes in the taste of crops, toxic effects on numerous beneficial organisms, development of resistant pest populations, incomplete decomposition by microorganisms and thus a too long persistence and accumulation in the soil as well as finally leaching into the groundwater and the accumulation in the food chain of humans and animals (Source: Umweltlexikon—www.umweltlexikon-online.de).

II. State of the Art

It is known that glycoside-cleaving enzyme preparations of the type of non-starch polysaccharide hydrolases are effective in the prophylaxis and therapy of plant pathogenic fungi. Here, a direct attack of the enzyme on the structures of the cell walls of the fungi, in particular of the oomycetes, is assumed (DE 10 2205 048 520, Biopract GmbH). However, these hydrolyses can also damage the cell wall of the plant and therefore, they are only partially suitable for plant protection.

The use of enzymes of the type of non-starch polysaccharide hydrolases for prophylaxis and therapy of fungal phytopathogens is also supported by a number of findings in other areas. For example, experience has been acquired in combating oocytes-based fish mycosis with complex enzyme preparations from *Trichoderma* spp. (WO 2004/002574 A1 Biopract GmbH).

U.S. Pat. No. 6,663,860 (Tvedten, Dec. 16, 2003) describes proteases as pesticide against, inter alia, insects, bacteria and fungi. However, a use in prophylaxis of fungal infestation in viticulture is not intended.

Furthermore, the combination of a pesticide and an enzyme, for example a protease, is described in various patent documents. Hereby, the described effect is rather based on the pesticide and not on the added enzyme alone (WO 2013/096383 A2, CN 103461383 A, WO 1997/047202 A1, WO 1990/003732 A1). Other patent documents describe the combination of detergents and enzymes (U.S. Pat. No. 7,393,528 B2), of plant extracts and proteins (WO 2001/030161 A1) as well as of surface-active substances and an enzyme (EP 184288 A1). Also these publications do not demonstrate that the enzyme itself is responsible for the pesticidal effect.

Finally, enzymes or enzyme combinations which show, inter alia, an anti-fungal or anti-bacterial effect, have been described in the past, for example a protease from plants (WO 1991/002459 A1), a protease from an earthworm (JP 2011177105A) or the culture supernatant of a *Bacillus* fermentation (JP 54073182 A).

None of the inventions mentioned above describes a comparably effective solution of the still existing problem of the infestation of crop plants by oomycetes and bacteria. The proteases described here provide a highly effective and simultaneously environmentally sound alternative to common plant protection products.

III. Objective of the Invention

The invention aims to develop a highly efficient means for controlling infections caused by fungi, in particular oomycetes, and bacterial infections in crop and ornamental plants that is harmless for the plant itself as well as for the ecosystem. The primary objective of the present invention is to develop a method for prophylaxis of infections of crop plants used in agriculture that are caused by phytopathogens. In particular, the problem of recognizing and preventing epidemics such as grapevine downy mildew in wine varieties early shall be solved. Providing appropriate means is also comprised by the invention.

This problem is solved by the measures described in the claims. The method according to the invention is characterized in that a concentrate and a ready for use solution, respectively, are produced, which contain a protease alone or a combination of proteases and δ-glucanases and/or chitinases. The quintessence of the invention is the surprising possibility to provide proteases alone as effective means for controlling infections in crops and ornamental plants.

Furthermore, the protective products can contain stabilizers, adhesive and wetting agents, which improve the application properties. Common rain stabilizers and UV stabilizers can also be included in these mixtures.

This mixture is applied by conventional application systems at fixed times, which are determined based on the weather condition, in a way that the whole plant is wetted. The application can be effected at temperatures between 4° C. and 34° C. and therefore during the whole growing season. In plant cultivation under glass, the application is largely independent from the weather conditions and temperatures range from 15° C. to 25° C. This mode of application ensures that the enzyme preparations are active and an infection of the plant by e.g. zoospores of phytopathogenic oomycetes or bacterial pathogens such as *Pseudomonas syringae* is prevented. The applied quantity per area has to be determined dependent on the crop plant. For example in vine growing, approximately 400 to 800 liter spray cocktail are currently applied on an area of one hectare. The described enzyme preparations are mixed in a way that conventional spraying technique can continued to be used.

The invention described constitutes a significant progress in comparison to currently established means and methods.

The advantages over the state of the art are described in the following:

In contrast to copper-containing preparations or other chemical plant protection products, the use of enzyme preparations is harmless for the ecosystem since the agent is completely degraded in the soil and not accumulated. Therefore, considerable environmental damages are prevented.

There are no phytotoxic reactions, since the applied proteases according to the invention do not attack the plant surface.

Proteases and other enzymes are effective during plant growth. They do not adhere at one location to the leaf structure but disperse in a liquid film on the surface.

The efficacy of the enzyme remains intact for a relevant period of several days despite of rain and UV radiation. This stability can be improved by suitable formulations if necessary.

Proteases, also called peptidases, cleave peptide bonds in proteins and so promote their degradation in peptides or amino acids. Proteases are divided into the following groups based on their mode of action: serine proteases, EC 3.4.21.-, (S), cysteine proteases (C), aspartic protease (A), metalloproteases (M), and unknown or so far unclassified proteases (Handbook of Proteolyse Enzymes, A. J. Barrett, N. D. Rawlings, J. F. Woessner (eds), Academic Press (1998)).

Proteases that are used according to the invention described are in particular serine proteases. The catalytic mechanism of this enzyme class is based on the nucleophilic hydroxyl group of the amino acid serine that can cleave peptide bonds. Respective enzymes can be gained from culture supernatants for example from microorganisms of the genera *Nocardiopsis* or *Bacillus*. The respective enzymes can also be produced recombinantly. Moreover, the effective proteases can be mutants, variants or fragments of the described enzymes that act analogous.

The activity of the proteases can be determined with every detection method in which a substrate is used that contains the respective peptide bonds (e.g. casein).

Surprisingly, it has been found that protease preparations, which are used for instance in animal feeding, prevent the infection of plants by phytopathogenic oomycetes and bacteria. Particularly zoospores that arise during the propagation cycle of oomycetes and that are responsible for the actual infection of the leaf tissue, are damaged irreversibly by the activity of these enzymes, and the infection of the so protected plant does not occur. The mode of action against bacterial infestation has not been elucidated so far. The significant impact of these enzymes was not expected to such extent since the modes of action and points of attack do not correspond to the mode of action described for β-glucanases or chitinases. The protective effect can be increased by a combination with β-glucanases and/or chitinases.

Commercially available preparations, which contain the proteases described, are for example Ronozyme®ProAct® (DSM Nutritional Products AG, examples 1-9: Prot III), which contains a serine protease from *Nocardiopsis* sp., or Alcalase® (Novozymes AG), which contains primarily one serine protease, Subtilisin A, from *Bacillus licheniformis*. Furthermore, select protease preparations that show a protective effect are those by the company Lumis Enzymes (PAP 2XS), which, as far as is known, contains papain from *papaya*, by the company Cyadic (Protease Plus, Protease AP Conc) and by the company AB Enzymes (BIOTOUCH ROC 250LC), which contains, as far as is known, a protease from *Trichoderma*.

Glucanases and chitinases are enzymes that can hydrolyze glucans or chitin. They are assigned to the enzyme class E.C. 3.2.1.-, which comprises glycosidases, i.e. enzymes that cleave O- and S-glycosidic bonds.

Following the characteristics of the specific disease, the enzyme against the leaf pathogens (e.g. downy mildew or *Pseudomonas syringae*) are applied by treating the aerial parts of the plant (e.g. by spraying) with concentrations of an enzyme preparation of 0.001% to 1%. Proteases and glycosylases are preferably used in different mixing ratios of the single enzymes.

The effect, according to the invention, of the enzyme preparations, which manifests itself in preventing the occurrence of the infection, is achieved by using proteases alone or as a mixture.

The enzymes are gained from culture supernatants of microorganisms. The components for the inactivation of the pathogen are preferably used in an aqueous milieu with a pH ranging from 4.5 to 8.5, preferably a pH ranging from 6.0 to 7.5. They are used at a water temperature of 4° C. to 34° C., preferably at 10° C. to 25° C.

In the following, the invention shall be illustrated by examples. The examples 1-7 demonstrate the use of proteases as protection against oomycetes while the examples 8 and 9 describe the protective effect against bacterial infections. Ronozyme®ProAct® (DSM Nutritionai Products AG) was used as protease III.

EXAMPLES

Protecting Crop Plants from Infection Caused by Omycetes

Example 1: Infection Suppressing Effect of Punctual Foliar Application of Protein Cleaving Enzyme Preparations Against *Plasmopara viticola* in Leaf Discs Leaf discs of the grapevine *Vitis vinifera* cv. Müller-Thurgau were treated once with different protein cleaving enzyme preparations (protease I, II and III) by spray application, so that the bottom side of the leaf of the used leaf discs was evenly wetted. The preparations contained a serine protease each, which was gained either from a species of the genus *Nocardiopsis* or *Bacillus*. The enzyme preparations used for the treatment were tested in concentrations ranging from 0.01% to 1% (v/v). The pH value of the preparations diluted in water ranged from 6 to 7.5. As control, the leaf discs were either sprayed with a copper-containing plant protection product or with water. 24 hours after treatment, the artificial infection of the leaf discs was performed with *Plasmopara viticola* (approximately 40000 spores per ml water), the pathogen that causes downy mildew in grapevine. Subsequently, the leaf discs were incubated on water agar plates at 22° C. for six days in a plant chamber with day-night rhythm.

The degree of infestation is calculated from the ratio of the total area of the leaf and the infected area of the leaf. For the analysis, image evaluation software was used, which distinguished between the total area (number of green pixel of the leaf discs at the beginning of the experiment) and the infected area (number of white pixels at the end of the experiment). Two of the tested protease preparations (I, Ill) as well as the copper-containing plant protection product (Cuprozin) prevented the infestation and the development of *Plasmopara viticola* effectively (0% infestation), the third preparation, protease II, prevented infestation only to some extent (38% infestation). However, leaf discs that were sprayed with water showed markedly infestation (see Table 2 and FIG. 1).

TABLE 2

Degree of infestation (%) calculated from the ratio of the total area of the leaf disc in relation to the infected area per leaf disc after treating the leaf discs with three different protease preparations (n = 36)

| | Degree of infestation (MW) | Standard deviation |
|---|---|---|
| $H_2O$ | 87% | 6% |
| Cuprozin | 0% | 1% |
| Protease I | 0% | 1% |
| Protease II | 38% | 28% |
| Protease III | 0% | 0% |

Example 2: Infection Suppressing Effect of Punctual Foliar Application of Combinations of Proteases, Chitinases and Glycoside-Cleaving Enzyme Preparations Against *Plasmopara viticola* in Leaf Discs Leaf discs of the grapevine *Vitis vinifera* cv. Müller-Thurgau were treated once with an enzyme combination consisting of protease, chitinase and β-glucanase in a mixing ration of 1:1:1 by spray application, so that the bottom side of the leaf of the used leaf discs was evenly wetted. The concentration of the enzyme preparations used was 0.1% (v/v) for each enzyme. The pH value of the in water diluted preparations ranged from 6 to 7.5. As control, the leaf discs were either sprayed with a copper-containing plant protection product or with water. 24 hours after treatment, the artificial infection of the leaf discs was performed with *Plasmopara viticola* (approximately 40000 spores per ml water), the pathogen that causes downy mildew in grapevine. Subsequently, the leaf discs were incubated on water agar plates at 22° C. for six days in a plant chamber with day-night rhythm.

The degree of infestation is calculated from the ratio of the total area of the leaf and the infected area of the leaf. For the analysis, image evaluation software was used which distinguished between the total area (number of green pixels of the leaf discs at the beginning of the experiment) and the infected area (number of white pixels at the end of the experiment). The development of *Plasmopara viticola* was effectively prevented on the leaf discs that were treated with the enzymes and the copper-containing plant protection product.

Example 3: Infection Suppressing Effect of Punctual Foliar Application of Protein Cleaving Enzyme Preparations Against *Plasmopara viticola* in Hothouse Plants Young vines of the variety *Vitis vinifera* cv. Müller-Thurgau were entirely single treated with a protein cleaving enzyme preparation (protease III) by means of a stationary application unit. The concentrations of the enzyme preparations used were 0.1%, 0.2% and 0.5% (v/v). The pH values of the spraying cocktails were adjusted between 6.5 and 7.5. As control, the further potted vines were either sprayed with a copper-containing plant protection product or with water. 24 hours after treatment with the protease preparation, the artificial infection of the leaves was performed with *Plasmopara viticola*, the pathogen that causes downy mildew in grapevine. Subsequently, the plants were incubated for one week in a greenhouse at 20° C. The infestation was determined by visual observation and given as the proportion (%) of diseased and necrotic alterations, respectively, at leaves and stems in relation to the total mass of the plant per replication (100%) and documented photographically. A scoring scale with the graduations 1, 5, 10, 15, 20, 25, 30, 40, 50, 90, 100% diseased alterations was used.

Figure 2:
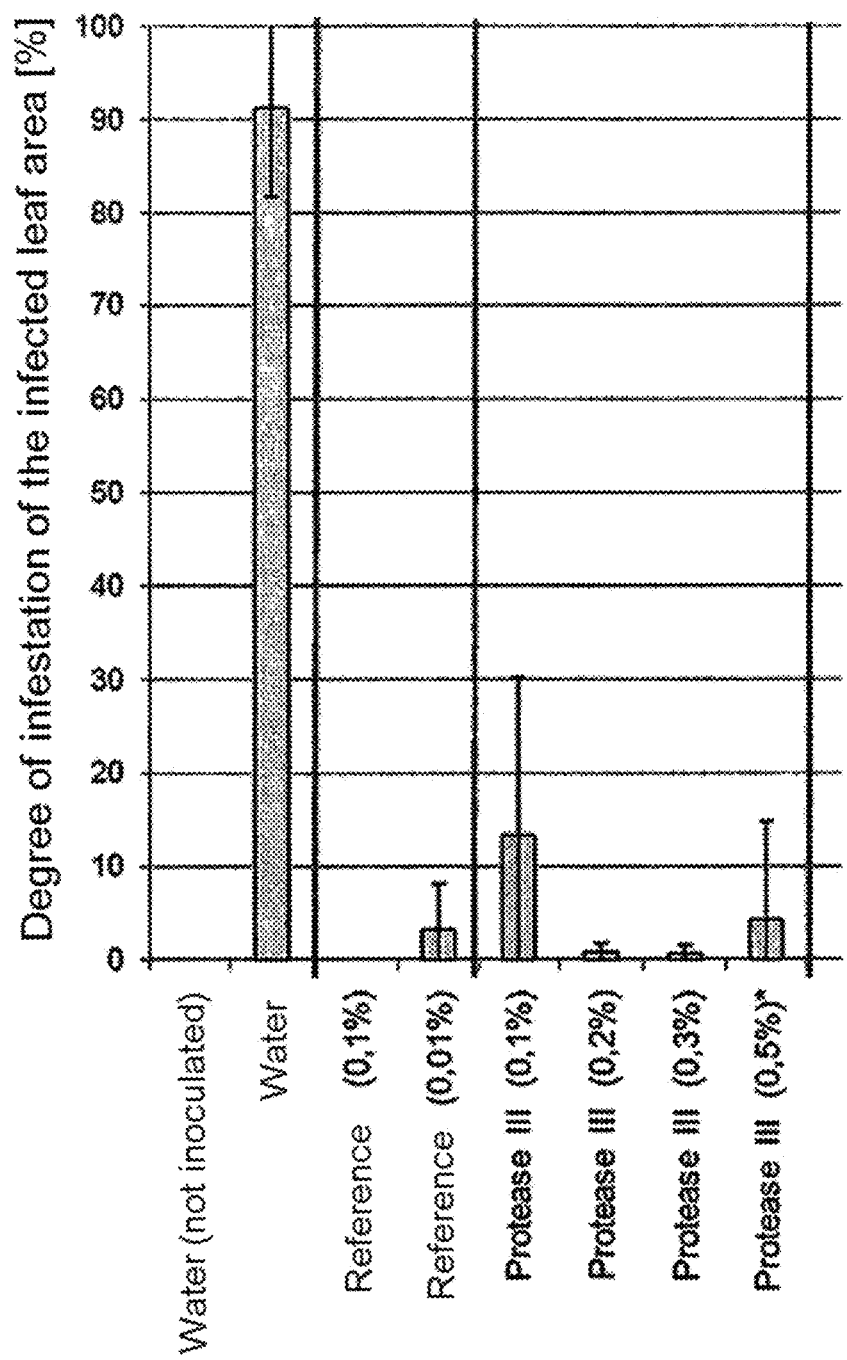
FIG. 2: Shows an efficacy test of Prot III at potted Müller-Thurgau vines. Presented is the degree of infestation of *P. viticola* in the treated variants protease III 0.01% to 0.5% in comparison to the internal standards water control and copper reference solution. The degree of infestation was effectively reduced by using Prot III. The increased infestation of plants treated with 0.5% Prot III (*) was caused by a spray shadow on a single leaf. The degree of infestation was calculated based on the proportional infestation of 6 individual plants with up to 6 leaves per variant.

The development and spread of *Plasmopara viticola* was effectively prevented on the plants that were treated with protease III and copper-containing plant protection products, while leaves that were sprayed with water showed high infestation (FIG. 2).

Example 4: Infection Suppressing Effect of Periodic Application of Protein Cleaving Enzyme Preparations Against *Plasmopara viticola* in Field Trials Whole vines of the variety *Vitis vinifera* cv. Blauer Spätburgunder were sprayed by means of a tunnel spraying machine with an enzyme-cleaving enzyme preparation (Prot III) during the growing season repeatedly at intervals of 8 to 14 days, so that the surface of the vines was evenly wetted. The concentration of the enzyme preparation used was 0.1% (v/v). The pH values of the spraying cocktails were adjusted between 6.5 and 7.5. For improved wetting of the leaves, a wetting agent (TREND 90) was further added.

At the end of the growing season, the degree of infestation and infestation frequency by downy mildew at leaves and grapes were scored. The development of *Plasmopara viticola* was effectively prevented at vines in open land.

Example 5: Infection Suppressing Effect of Protein Cleaving Enzyme Preparations Against the Pathogen that Causes Late Blight (*Phytophthora infestans*) in Tomato Plants Tomatoes of the variety Red robin were sprayed at 4-leaf stage with the protease preparation (protease III, 0.1% (v/v)). The pH values of the spraying cocktails were adjusted between 6.5 and 7.5. As additional variants, common wetting agents (T/S forte, Biomaxima, Nufilm) were added with a concentration of 0.02% (v/v) to the protease solution. The commercial copper preparation Atempo and water served as internal controls. Per variation, 5 replicates with one plant each were prepared.

24 hours after applying the enzymes, the artificial inoculation with the pathogen *Phytophthora infestans* was performed with a sporangia concentration of 80 000 spores per ml. For each plant, 6 ml suspension were applied. The plants were placed in the incubator at approximately 16° C. and 100% relative humidity without light. After 24 hours, a lighting rhythm of 16:8 hours was set and the humidifier was turned off. Scoring was performed 6 days after infection. The infestation was determined by visual observation and given as proportion (%) of diseased or necrotic alterations at leaves and stems in relation to the total mass of the plant and documented photographically (Tab. 3).

TABLE 3

Infestation by *Phytophtora infestans* and efficiency of the protease preparation

| No. | Variant | Infestation [%] Mean (Standard deviation) | Efficiency [%] |
|---|---|---|---|
| 1 | Protease III | 12.00 (2.74) | 87.50 |
| 2 | Protease III + T/S-Forte | 18.00 (2.74) | 81.25 |
| 3 | Protease III + BioMaxima | 11.00 (5.48) | 88.54 |
| 4 | Protease III + Nufilm P | 12.00 (2.74) | 87.50 |
| 5 | Atempo (copper-containing reference) | 1.80 (1.79) | 98.13 |
| 6 | Water control | 96.00 (5.48) | 0.00 |

Example 6: Infection Suppressing Effect of Protein Cleaving Enzyme Preparations Against *Pseudoperonospora cubensis* in Cucumber Plants Cucumber plants were grown in a climatic chamber. For proving the protective effect of proteases, the bottom sides of the leaves were sprayed with approximately 6 ml of the protease preparation (Prot III), which was an aqueous solution with a concentration of 0.1%. The pH values of the spraying cocktails were adjusted between 6.5 and 7.5. A common copper preparation (Cuprozin Progress) and water served as controls. Per variation, 6 replicates with one plant each were prepared. One day after applying the enzymes, the trial plants were infected with *Pseudoperonospora cubensis* (75 000 spores per ml). Incubation was performed at room temperature in a greenhouse at a relative humidity of more than 95%. During the first 48 hours, the plants were incubated in the dark, then, the plants were kept in a day-night rhythm of 16/8 hours. Scoring was performed 10 days after infection. Thereby, the proportional infestation of the plants was determined. Infestation could be reduced to less than 4% by using the preparation Prot III (Tab. 4).

TABLE 4

| No. | Variant | Infestation [%] Mean (Standard deviation) | Efficiency [%] |
|---|---|---|---|
| 1 | Protease III | 3.6 (0.4) | 94.1 |
| 5 | Cuprozi Progress (copper-containing standard) | 9.0 (4.7) | 85.2 |
| 6 | Water | 60.4 (11.9) | 0.00 |

Example 7: Comparison of the Infection Suppressing Effect of Different Protease Preparations Against *Pseudoperonospora cubensis* in Cucumber Plants Cucumber plants were grown in a climatic chamber. For the comparison of the efficiency of different protease preparations, the bottom sides of the leaves were sprayed with approximately 6 ml of each protease preparation (Prot III-Prot IX), which was an aqueous solution with a concentration of 0.1%. The pH values of the spraying cocktails were adjusted between 6.5 and 7.5. A common copper preparation (Cuprozin Progress) and water served as controls. Per variation, 6 replicates with one plant each were prepared. One day after applying the enzymes, the trial plants were infected with *Pseudoperonospora cubensis*. Incubation was performed at room temperature in a greenhouse at a relative humidity of more than 95%. During the first 48 hours, the plants were incubated in the dark, then, the plants were kept in a day-night rhythm of 16/8 hours. Scoring was performed 10 days after infection. Hereby, the proportional infestation of the plants was determined. The efficiency of the individual preparations is presented in table 5. The preparation with the best effect was protease III. The proteases IV, VIII and IX have a similar effect. As far as known, the organisms of which the respective protease originated, is stated.

TABLE 5

Overview of the protease preparations that were used in the experiment as well as the infestation and the respective efficiencies

| Sample ID | Origin | Product | Infestation [%] Mean (Standard deviation) | Efficiency [%] |
|---|---|---|---|---|
| Prot III | Nocardiopsis | Ronozyme ProAct | 0.4 (0.4) | 98.6 |
| Prot IV | Bacillus | Alcalase | 0.5 (0.4) | 98.3 |
| Prot V | Bacillus | Savinase | 9.8 (4.8) | 65.8 |
| Prot VI | Aspergillus | Flavourzyme | 35.0 (21.5) | — |
| Prot VIII | Papaya | PAP 2X5 | 0.8 (0.3) | 97.2 |
| Prot IX | Bacillus | Protease AP Conc | 1.0 (0.6) | 98.5 |
| Copper-containing fungicide | — | Cuprozin Progress | 7.4 (6.2) | 74 |

Protecting Crop Plants from Infection Caused by Bacteria

Example 8: Plating Experiment for Proving the Growth Inhibiting Effect of Proteases Against *Clavibacter michiganensis*

Figure 3:
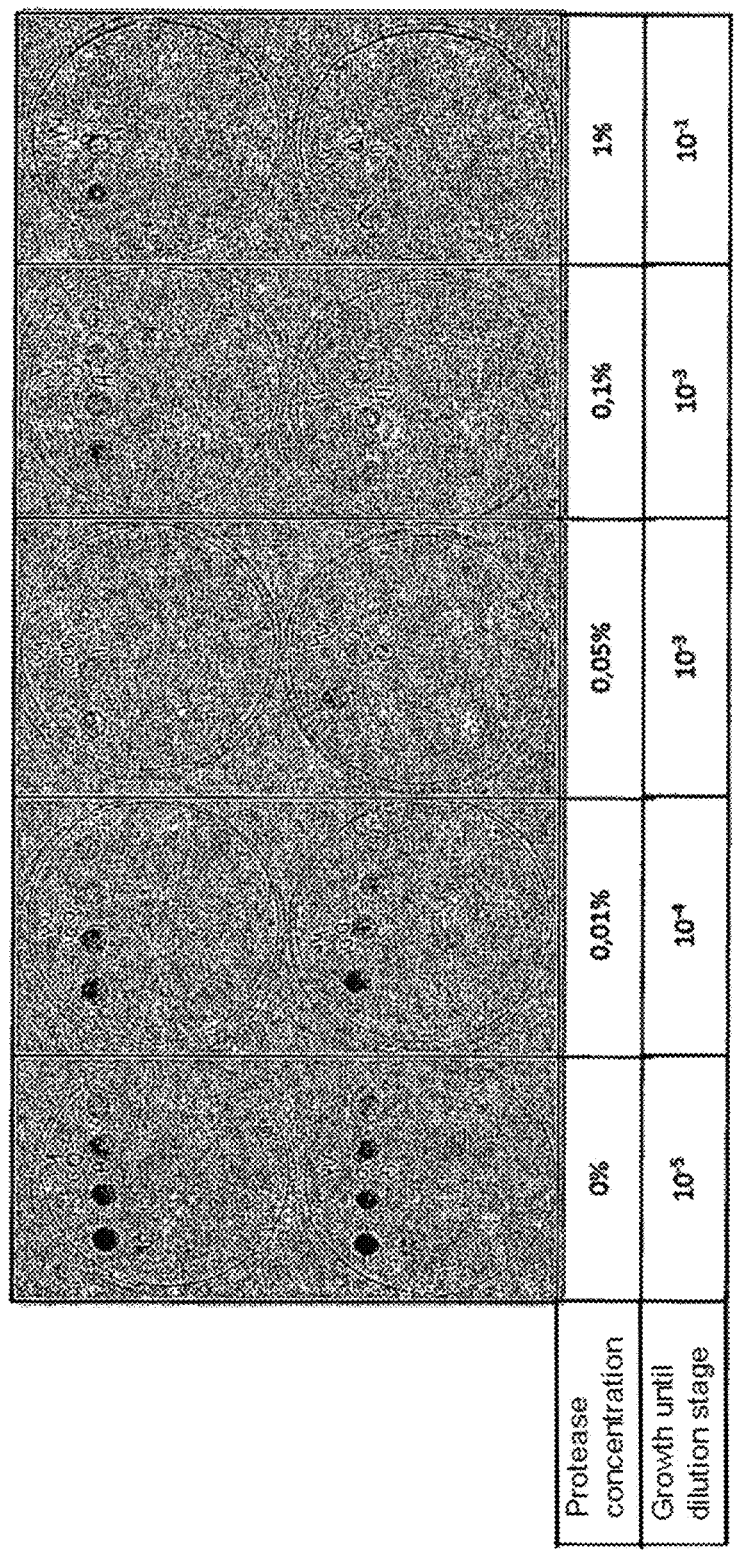
FIG. 3: Shows the presentation of the inhibiting effect of protease III on the growth of *C. michiganensis*. Presented are dilution series of a bacterial culture of different concentrations of protease III. Numbers below the agar plates indicate the dilution up to which the bacteria grew.

A culture of *Clavibacter michiganensis* was grown until late log phase and accordingly diluted to $OD_{600}$ nm=1.0 in a 10 nM NaCl solution. This starting culture was plated in 12 dilutions ranging from $10^{-1}$ to $10^{-12}$ on nutrient agar each which contained the preparation protease III in concentrations of 0.01-1%. Two control plates were free of protease III and showed the maximal growth of *Clavibacter michiganensis* at the given conditions (FIG. 3, left: $10^{-5}$). The bacterial growth was effectively inhibited at protease concentrations starting at 0.05% since only the most concentrated dilutions were grown ($10^{-1}$ to $10^{-3}$, see FIG. 3). The high potential of protease III as plant protection means for controlling bacterial wilt in tomato (*Clavibacter michiganensis* subsp. *michiganensis*) becomes apparent by this experiment.

Example 9: Protecting Tomato Plants from Infections Caused by *Pseudomonas syringae*

For this experiment, tomato plants of the variety "Red Robin" were sprayed with a 0.1 protease solution (protease III) with and without the addition of an adhesive agent (NufilmP) and incubated at 22° C. for 24 hours. The pH value of the spraying cocktail was adjusted between 6.5 and 7.5. As controls served 4 plants each that were sprayed with tap water and a mock solution, respectively. 24 hours after applying the enzymes, plants were infected with *Pseudomonas syringae*.

Figure 4:
FIG. 4: Shows the proliferation of *P. syringea* bacteria in foliar segments of tomato within 21 days after inoculation. Tomato plants were mock-treated (blank) and sprayed with a protease III or protease III in Nufilm-P, respectively. The colony forming units (CFU) were isolated from 0.7 cm$^2$ foliar segments and counted after an incubation of 48 hours.

The first samples of 0.7 cm² large foliar segments were taken two hours after inoculation, further samples were taken at day 7, 14 and 21 after inoculation. For analysis 4 different single leaves were taken from each of 4 different plants, and from each of these four different single leaves 4 foliar segments were taken for analysis. At the beginning, the number of colony forming units (CFU) per foliar segment was $1 \times 10^3$. In the control (water), the number of CFU increased to $1 \times 10^6$ CFU per foliar segment within three weeks. Plants that were treated with protease III remained at a constant level ($10^3$ CFU per leaf) in the first two weeks. After three weeks, the number of CFU per leaf on leaves treated with protease was significantly decreased to 10 CFU per foliar segment (FIG. 4). The protease used was considerably more effective than the mock substance.

REFERENCES

DE LA FUENTE, L. and BURDMAN, S. 2011. Pathogenic and beneficial plant-associated bacteria. In Agricultural Sciences, [Ed. Rattan Lal], in Encyclopedia of Life Support Systems (EOLSS), Developed under the Auspices of the UNESCO, Eolss Publishers, Oxford, UK, [http://www.eolss.net]

DE MARCO, J. L; VALADARES-INGLIS, M. C. and CR. FELIX, 2003: Production of hydrolytic enzymes by *Trichoderma* isolates with antagonistic activity against *Crinipellis perniciosa*, the causal agent of witches' broom of cocoa. Brazilian J. Microbiol. 34, 33-38

KASSEMEYER H.-H. (2004) Forschungsvorhaben für das Programm des Bundesministeriums für Verbraucherschutz, Ernährung und Landwirtschaft zur Förderung von Forschungs- und Entwicklungsvorhaben sowie zum Technologie- und Wissenstransfer im ökologischen Landbau. "Innovationen zur Verbesserung der Rahmenbedingungen für den ökologischen Weinbau. Erarbeitung von wissenschaftlichen Ansätzen zur biologischen Kontrolle der Rebenperonospora und für Strategien zu deren Regulierung im ökologischen Weinbau", Projektnummer 020E269, Staatliches Weinbauinstitut Freiburg KUDO, S. and C. TESHIMA, 1991: Enzyme activities and antifungal action of fertilization envelope extract from fish eggs. The Journal of Experimental Zoology 259, 392-398

KUDO, S., 1992: Enzymatic basis for protection of fish embryos by the fertilization envelope. Experientia 48, 277-281

KUDO, S., 2000: Enzymes responsible for the bactericidal effect in extracts of vitelline and fertilization envelopes of rainbow trout eggs. Zygote 8, 257-265

KÜCÜK, C. and M. KIVANC 2002: Isolation of *Trichoderma* spp. and determination of their antifungal, biochemical and physiological features. Türk. J. Biol. 27, 247-253

MALATHRAKIS, N. E., GOUMAS, D. E. 1999: Fungal and bacterial diseases. See Ref. 4 pp. 34-47.

MÜNCH, S., NEUHAUS, J. M., BOLLER, T., KEMMERLING, B. and K. H. KOGEL 1997: Expression of ß-1,3-glucanase and chitinase in healthy, stem rust-affected and elicitor-treated near-isogenic wheat lines showing Sr5 or Sr24-specific rust resistance. Planta 201, 235-244

OERKE, E. CH. und U. STEINER 1996: Ertragsverluste und Pflanzenschutz: Die Anbausituation für die wirtschaftlich wichtigsten Kulturen. Schriftenreihe der deutschen Phytomedizinischen Gesellschaft, Eugen Ulmer GmbH & Co., Stuttgart PAULITZ, T. C. BELANGER, R. R. 2001: Biological control in greenhouse Systems. Annu. Rev. Phytopathol. 39, 103-133

POWELL, K. A., JUTSUM, A. R. (1993) Technical and commercial aspects of biocontrol products. Pestic. Sei. 37, 315-321.

SCALA F., S. L. WOO, I. GARCIA, A. ZOINA, E. FILIPPONE, J.-A. PINTOR-TORO, G. DEL SORBO, B. ALOJ and M. LORITO. 1998. Transgenic tobacco and potato plants expressing antifungal genes from *Trichoderma* are resistant to several plant pathogenic fungi. 7th International Congress of Plant Pathology, Aug. 9-16, 1998, Edinburgh, Scotland, Offered Papers Abstracts—Volume 3: May 3, 2010.

WO 2004/002574 A1 Biopract GmbH, Berlin; LEIBNIZ-Institut für Gewässerökologie und Binnenfischerei im Forschungsverbund Berlin e.V. Verfahren zur Prophylaxe und Therapie von Mykosen bei Fischen und Wirbellosen und deren Entwicklungsstadien. (expired)

DE 10 2205 048 520 Biopract GmbH, Berlin GmbH, Institut für Gemüse- und Zierpflanzenbau Großbeeren/Erfurt. Verfahren zur Prophylaxe und Therapie von Mykosen bei Nutz- und Zierpflanzen sowie bei Gehölzen, insbesondere in hydroponischen Systemen, Jul. 10, 2007

The invention claimed is:

1. A method for prophylaxis of infection by *Plasmopara viticola* in crops and ornamental plants, comprising spraying plants with an aqueous solution of a bacterial serine protease, characterized in that said bacterial serine protease is derived from *Bacillus* sp. or *Nocardiopsis* sp.

2. The method according to claim 1, characterized in that said aqueous solution of a bacterial serine protease for the control of pathogens is applied at a dosage of 0.001-% to 1-%.

3. The method according to claim 1, characterized in that a time interval treatment of the plants is performed by spraying aerial parts of the plants.

4. The method according to claim 1, characterized in that said aqueous solution of a bacterial serine protease is applied at a pH of 4.0 to 8.0.

5. The method according to claim 1, characterized in that said aqueous solution of a bacterial serine protease is applied at temperatures of 4° C. to 34° C.

6. The method according to claim 1, characterized in that said aqueous solution of a bacterial serine protease is formulated with adhesive and wetting agents as well as stabilizers.

7. The method according to claim 1, characterized in that said aqueous solution consists of said bacterial serine protease.

8. The method, according to claim 1, characterized in that said aqueous solution consists of a combination of bacterial serine proteases.

9. A method for suppressing infections by *Phytophthora infestans, Pseudoperonospora cubensis, Pseudomonas syringae* or *Clavibacter michiganensis* in crops and ornamental plants, comprising spraying plants with an aqueous solution consisting essentially of a bacterial serine protease, characterized in that said bacterial serine protease is derived from *Bacillus* sp. or *Nocardiopsis* sp.

10. The method according to claim 9, characterized in that said aqueous solution of a bacterial serine protease for the control of pathogens is applied at a dosage of 0.001% to 1%.

11. The method according to claim 9, characterized in that a time interval treatment of the plants is performed by spraying aerial parts of the plants.

12. The method for according to claim 9, characterized in that said aqueous solution of a bacterial serine protease is applied at a pH of 4.0 to 8.0.

13. The method according to claim 9, characterized in that said aqueous solution of a bacterial serine protease is applied at temperatures of 4° C. to 34° C.

14. The method according to claim 9, characterized in that said aqueous solution of a bacterial serine protease is formulated with adhesive and wetting agents as well as stabilizers.

15. The method according to claim 9, characterized in that said aqueous solution consists of said bacterial serine protease.

16. The method according to claim 9, characterized in that said aqueous solution consists of a combination of bacterial serine proteases.

* * * * *